(12) United States Patent
Orban, III et al.

(10) Patent No.: US 8,192,460 B2
(45) Date of Patent: Jun. 5, 2012

(54) ANNULAR SUPPORT STRUCTURES

(75) Inventors: Joseph P. Orban, III, Norwalk, CT (US); Timothy Nolan, South Salem, NY (US)

(73) Assignee: Tyco Healthcare Group LP, Mansfield, MA (US)

( * ) Notice: Subject to any disclaimer, the term of this patent is extended or adjusted under 35 U.S.C. 154(b) by 214 days.

(21) Appl. No.: 12/624,715

(22) Filed: Nov. 24, 2009

(65) Prior Publication Data

US 2010/0065607 A1 Mar. 18, 2010

Related U.S. Application Data

(63) Continuation of application No. 11/872,778, filed on Oct. 16, 2007, now Pat. No. 7,951,166, which is a continuation of application No. 10/516,435, filed as application No. PCT/US03/19331 on Jun. 17, 2003, now Pat. No. 7,744,627.

(60) Provisional application No. 60/389,567, filed on Jun. 17, 2002.

(51) Int. Cl.
*A61B 17/08* (2006.01)
*A61B 17/10* (2006.01)

(52) U.S. Cl. ............... 606/215; 606/151; 227/175.1

(58) Field of Classification Search ............ 606/151, 606/214, 215, 219, 220, 142; 227/175.1; 602/49–52, 41
See application file for complete search history.

(56) References Cited

U.S. PATENT DOCUMENTS

| | | |
|---|---|---|
| 2,514,844 A | 7/1950 | Cohen |
| 3,022,810 A | 2/1962 | Lambe |
| 3,054,406 A | 9/1962 | Usher |
| 3,124,136 A | 3/1964 | Usher |
| 3,753,266 A | 8/1973 | Ceniceros |
| 4,200,098 A | 4/1980 | Ayer et al. |
| 4,203,439 A | 5/1980 | Theeuwes |
| 4,231,407 A | 11/1980 | James |
| 4,286,587 A | 9/1981 | Wong |
| 4,347,847 A | 9/1982 | Usher |
| 4,354,628 A | 10/1982 | Green |
| 4,452,245 A | 6/1984 | Usher |
| 4,605,730 A | 8/1986 | Shalaby et al. |
| 4,655,221 A | 4/1987 | Devereux |
| 4,765,986 A | 8/1988 | Liedtke |
| 4,796,603 A | 1/1989 | Dahlke et al. |

(Continued)

FOREIGN PATENT DOCUMENTS

DE 1 99 24 311 11/2000

(Continued)

OTHER PUBLICATIONS

European Search Report for EP 09161658.1-1269.8-2318 date of completion is Jul. 2, 2009 (3 pages).

(Continued)

*Primary Examiner* — Julian Woo

(57) ABSTRACT

Reinforcing lumen rings are configured and adapted for use in conjunction with a circular endoscopic stapling instrument having a staple cartridge assembly and an anvil assembly. The reinforcing lumen rings maintain anastomotic lumen, e.g. as formed by the circular endoscopic stapling apparatus, in an open condition. The reinforcing lumen rings can include an annular ring having an outer terminal edge and an inner terminal edge, the outer terminal edge having a diameter which is substantially equal to an outer diameter of the staple cartridge assembly and the inner terminal edge having a diameter which is substantially equal to an inner diameter of the staple cartridge assembly.

14 Claims, 7 Drawing Sheets

U.S. PATENT DOCUMENTS

| | | |
|---|---|---|
| 4,834,090 A | 5/1989 | Moore |
| 4,838,884 A | 6/1989 | Dumican et al. |
| 4,909,972 A | 3/1990 | Britz |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,065,929 A | 11/1991 | Schulze et al. |
| 5,104,025 A * | 4/1992 | Main et al. ................. 227/175.1 |
| 5,160,344 A | 11/1992 | Werton |
| 5,205,459 A | 4/1993 | Brinkerhoff et al. |
| 5,263,629 A | 11/1993 | Trumbull et al. |
| 5,314,471 A | 5/1994 | Brauker et al. |
| 5,344,454 A | 9/1994 | Clarke et al. |
| 5,344,459 A | 9/1994 | Swartz |
| 5,392,979 A | 2/1995 | Green et al. |
| 5,397,324 A | 3/1995 | Carroll et al. |
| 5,425,745 A | 6/1995 | Green et al. |
| 5,441,193 A | 8/1995 | Gravener |
| 5,441,507 A | 8/1995 | Wilk et al. |
| 5,468,253 A | 11/1995 | Bezwada et al. |
| 5,503,638 A | 4/1996 | Cooper et al. |
| 5,542,594 A | 8/1996 | McKean et al. |
| 5,549,628 A | 8/1996 | Cooper et al. |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,762,256 A | 6/1998 | Mastri et al. |
| 5,766,188 A | 6/1998 | Igaki |
| 5,766,223 A | 6/1998 | Johnson |
| 5,769,892 A | 6/1998 | Kingwell |
| 5,782,396 A | 7/1998 | Mastri et al. |
| 5,782,868 A | 7/1998 | Moore et al. |
| 5,788,977 A | 8/1998 | Aguadisch et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,895,412 A | 4/1999 | Tucker |
| 5,895,415 A | 4/1999 | Tucke |
| 5,902,312 A | 5/1999 | Frater et al. |
| 5,908,427 A | 6/1999 | McKean et al. |
| 5,915,616 A | 6/1999 | Viola et al. |
| 5,918,384 A | 7/1999 | Meschan |
| 5,931,847 A | 8/1999 | Bittner et al. |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov et al. |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,099,551 A | 8/2000 | Gabbay |
| 6,149,667 A | 11/2000 | Hovland et al. |
| 6,155,265 A | 12/2000 | Hammerslag |
| 6,210,439 B1 | 4/2001 | Firmin et al. |
| 6,214,020 B1 | 4/2001 | Mulhauser et al. |
| 6,241,139 B1 | 6/2001 | Shelton et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,436,030 B2 | 8/2002 | Rehil |
| 6,454,780 B1 | 9/2002 | Wallace |
| 6,461,368 B2 | 10/2002 | Fogarty et al. |
| 6,503,257 B2 | 1/2003 | Grant et al. |
| 6,514,283 B2 | 2/2003 | DiMatteo et al. |
| 6,517,566 B1 | 2/2003 | Hovland et al. |
| 6,551,356 B2 | 4/2003 | Rousseau |
| 6,592,597 B2 | 7/2003 | Grant et al. |
| 6,638,285 B2 | 10/2003 | Gabbay |
| 6,652,594 B2 | 11/2003 | Francis et al. |
| 6,656,193 B2 | 12/2003 | Grant et al. |
| 6,669,735 B1 | 12/2003 | Pelissier |
| 6,677,258 B2 | 1/2004 | Carroll et al. |
| 6,685,714 B2 | 2/2004 | Rousseau |
| 6,704,210 B1 | 3/2004 | Myers |
| 6,712,853 B2 | 3/2004 | Kuslich |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,773,458 B1 | 8/2004 | Brauker et al. |
| 6,927,315 B1 | 8/2005 | Heinecke et al. |
| 7,128,748 B2 | 10/2006 | Mooradian et al. |
| 7,147,138 B2 | 12/2006 | Shelton, IV |
| 7,434,717 B2 | 10/2008 | Shelton, IV et al. |
| 7,438,209 B1 | 10/2008 | Hess et al. |
| 7,547,312 B2 | 6/2009 | Bauman et al. |
| 7,559,937 B2 | 7/2009 | de la Torre et al. |
| 7,604,151 B2 | 10/2009 | Hess et al. |
| 7,665,646 B2 | 2/2010 | Prommersberger |
| 7,744,627 B2 | 6/2010 | Orban, III et al. |
| 7,793,813 B2 | 9/2010 | Bettuchi |
| 7,823,592 B2 | 11/2010 | Bettuchi et al. |
| 7,845,533 B2 | 12/2010 | Marczyk et al. |
| 7,845,536 B2 | 12/2010 | Viola et al. |
| 7,909,224 B2 | 3/2011 | Prommersberger |
| 2002/0016626 A1 | 2/2002 | DiMatteo et al. |
| 2002/0019187 A1 | 2/2002 | Carroll et al. |
| 2002/0052622 A1 | 5/2002 | Rousseau |
| 2002/0091397 A1 | 7/2002 | Chen |
| 2002/0133236 A1 | 9/2002 | Rousseau |
| 2002/0138152 A1 | 9/2002 | Francis et al. |
| 2002/0151911 A1 | 10/2002 | Gabbay |
| 2002/0165559 A1 | 11/2002 | Grant et al. |
| 2002/0165562 A1 | 11/2002 | Grant et al. |
| 2002/0165563 A1 | 11/2002 | Grant et al. |
| 2002/0177859 A1 | 11/2002 | Monassevitch et al. |
| 2003/0065345 A1 | 4/2003 | Weadock |
| 2003/0065346 A1 | 4/2003 | Evens et al. |
| 2003/0083676 A1 | 5/2003 | Wallace |
| 2003/0088256 A1 | 5/2003 | Conston et al. |
| 2003/0105510 A1 | 6/2003 | DiMatteo et al. |
| 2003/0114866 A1 | 6/2003 | Ulmsten et al. |
| 2003/0120284 A1 | 6/2003 | Palacios |
| 2003/0167064 A1 | 9/2003 | Whayne |
| 2003/0181927 A1 | 9/2003 | Wallace |
| 2003/0183671 A1 | 10/2003 | Mooradian et al. |
| 2003/0208231 A1 | 11/2003 | Williamson, IV et al. |
| 2004/0034377 A1 | 2/2004 | Sharkawy et al. |
| 2004/0092960 A1 | 5/2004 | Abrams et al. |
| 2004/0093029 A1 | 5/2004 | Zubik et al. |
| 2004/0107006 A1 | 6/2004 | Francis et al. |
| 2004/0116945 A1 | 6/2004 | Sharkawy et al. |
| 2004/0142621 A1 | 7/2004 | Carroll et al. |
| 2004/0172048 A1 | 9/2004 | Browning |
| 2004/0209059 A1 | 10/2004 | Foss |
| 2004/0215214 A1 | 10/2004 | Crews et al. |
| 2004/0215219 A1 | 10/2004 | Eldridge et al. |
| 2004/0215221 A1 | 10/2004 | Suyker et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021026 A1 | 1/2005 | Baily |
| 2005/0021053 A1 | 1/2005 | Heinrich |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0228446 A1 | 10/2005 | Mooradian et al. |
| 2005/0245965 A1 | 11/2005 | Orban et al. |
| 2006/0004407 A1 | 1/2006 | Hiles et al. |
| 2006/0085034 A1 | 4/2006 | Bettuchi |
| 2006/0135992 A1 | 6/2006 | Bettuchi et al. |
| 2006/0173470 A1 | 8/2006 | Oray et al. |

| | | |
|---|---|---|
| 2006/0178683 A1 | 8/2006 | Shimoji et al. |
| 2006/0212050 A1 | 9/2006 | D'Agostino et al. |
| 2006/0271104 A1 | 11/2006 | Viola et al. |
| 2007/0034669 A1 | 2/2007 | de la Torre et al. |
| 2007/0049953 A2 | 3/2007 | Shimoji et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0246505 A1 | 10/2007 | Pace-Floridia et al. |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0078739 A1 | 3/2009 | Viola |
| 2009/0095791 A1 | 4/2009 | Bauman et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0065606 A1 | 3/2010 | Stopek |
| 2010/0065607 A1 | 3/2010 | Orban, III et al. |
| 2010/0072254 A1 | 3/2010 | Aranyi et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0236707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |

FOREIGN PATENT DOCUMENTS

| | | |
|---|---|---|
| DE | 1 99 24 311 A1 | 11/2000 |
| DE | 19924311 | 11/2000 |
| EP | 0 594 148 | 4/1994 |
| EP | 0 594 148 A1 | 4/1994 |
| EP | 0 327 022 B1 | 4/1995 |
| EP | 0 667 119 A1 | 8/1995 |
| EP | 1 064 883 A1 | 1/2001 |
| EP | 1 256 317 A2 | 11/2002 |
| EP | 1 520 525 | 4/2005 |
| EP | 1 520 525 A1 | 4/2005 |
| EP | 1 621 141 A21 | 2/2006 |
| EP | 1 759 640 A2 | 3/2007 |
| EP | 2 005 894 A2 | 12/2008 |
| EP | 2 005 895 A2 | 12/2008 |
| FR | 2778081 A | 11/1999 |
| JP | 06327683 A | 11/1994 |
| WO | WO 90/05489 | 5/1990 |
| WO | WO 90/05489 A1 | 5/1990 |
| WO | WO 97/01989 A1 | 1/1997 |
| WO | WO 97/13463 A1 | 4/1997 |
| WO | WO 98/17180 | 4/1998 |
| WO | WO 98/17180 A1 | 4/1998 |
| WO | WO 98/38923 A | 9/1998 |
| WO | WO 99/45849 | 9/1999 |
| WO | WO 99/45849 A1 | 9/1999 |
| WO | WO 03/082126 A1 | 10/2003 |
| WO | WO 03/105698 A2 | 12/2003 |
| WO | WO 2006/023578 | 3/2006 |
| WO | WO 2006/023578 A2 | 3/2006 |
| WO | WO 2006/044490 | 4/2006 |
| WO | WO 2006/044490 A2 | 4/2006 |
| WO | WO 2006/083748 A1 | 8/2006 |
| WO | WO 2008/057281 A2 | 5/2008 |
| WO | WO 2008/109125 A1 | 9/2008 |

OTHER PUBLICATIONS

International Search Report from application EP 06016962.0 dated Jan. 3, 2007.

International Search Report from Application PCT/US05/36740 mailed Mar. 23, 2007.

International Search Report from Application EP 08251779 dated Jul. 23, 2008.

International Search Report corresponding to European Application No. EP 06 00 4598, completed on Jun. 22, 2006; 2 pages.

International Search Report corresponding to European Application No. EP 06 01 6962.0, completed on Jan. 3, 2007 and mailed on Jan. 11, 2007; 10 pages.

International Search Report corresponding to International Application No. PCT/US05/36740, completed on Feb. 20, 2007 and mailed on Mar. 23, 2007; 8 pages.

International Search Report corresponding to International Application No. PCT/US2008/002981, completed on Jun. 9, 2008 and mailed on Jun. 26, 2008; 2 pages.

International Search Report corresponding to European Application No. EP 08 25 1779, completed on Jul. 14, 2008 and mailed on Jul. 23, 2008; 5 pages.

International Search Report corresponding to European Application No. EP 08 25 1989.3, completed on Mar. 11, 2010 and mailed on Mar. 24, 2010; 3 pages.

International Search Report corresponding to European Application No. EP 05 80 4382.9, completed on Oct. 5, 2010 and mailed on Oct. 12, 2010; 3 pages.

International Search Report corresponding to European Application No. EP 10 25 1437.9, completed on Nov. 22, 2010 and mailed on Dec. 16, 2010; 3 pages.

International Search Report corresponding to European Application No. EP 09 25 2897.5, completed on Feb. 7, 2011 and mailed on Feb. 15, 2011; 3 pages.

International Search Report corresponding to European Application No. EP 10 25 0715.9, completed on Jun. 30, 2010 and mailed on Jul. 20, 2010; 3 pages.

International Search Report corresponding to European Application No. EP 10 25 0642.5, completed on Mar. 25, 2011 and mailed on Apr. 4, 2011; 4 pages.

* cited by examiner

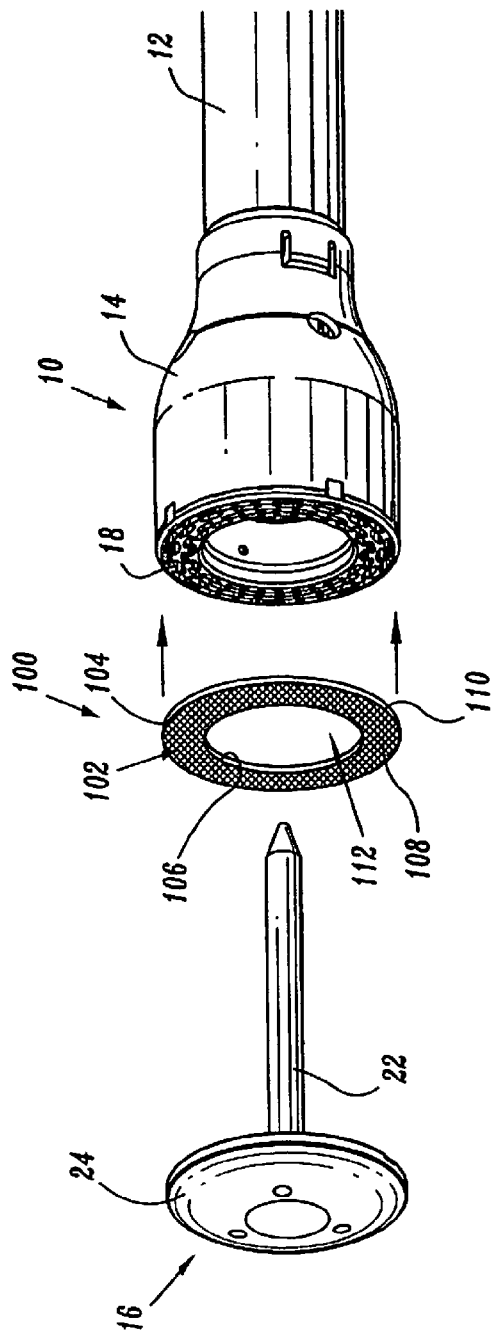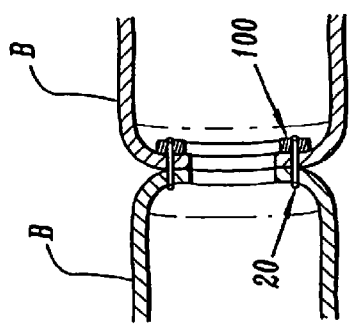

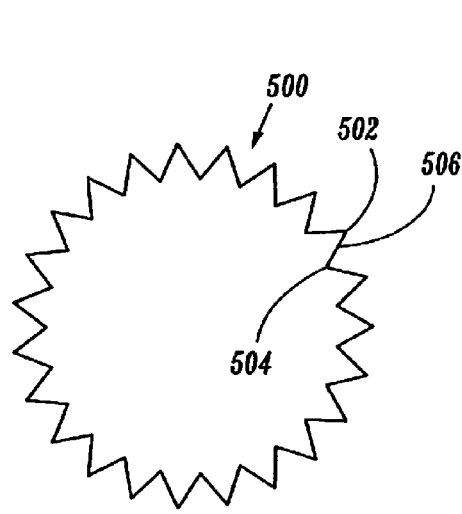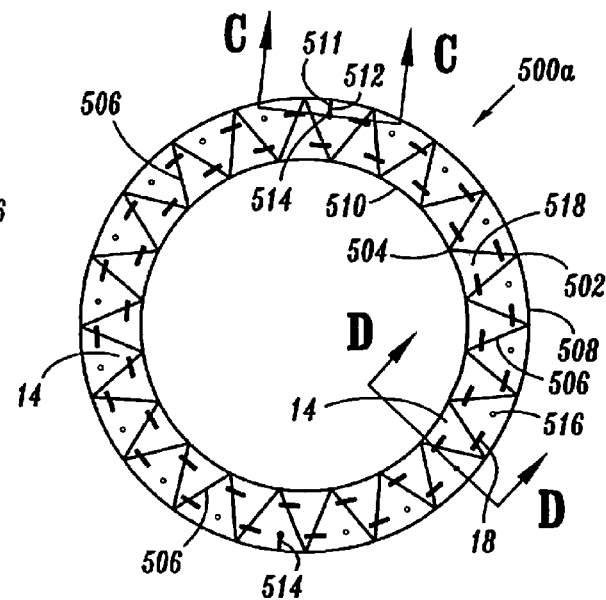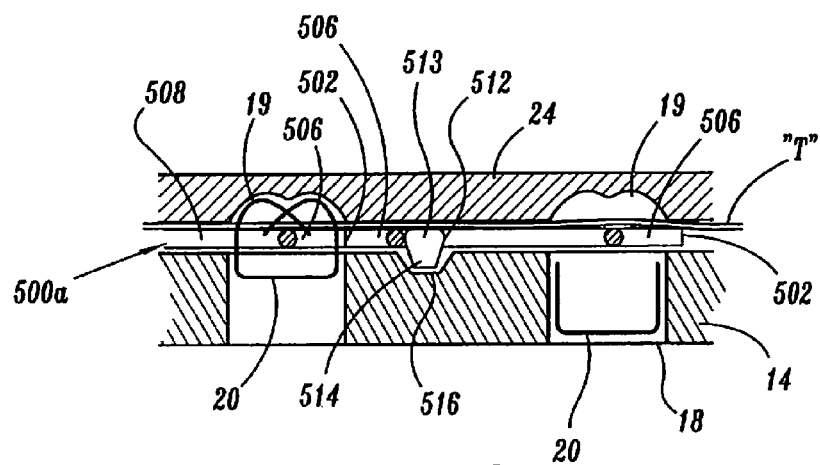
FIG. 11
FIG. 12
FIG. 13

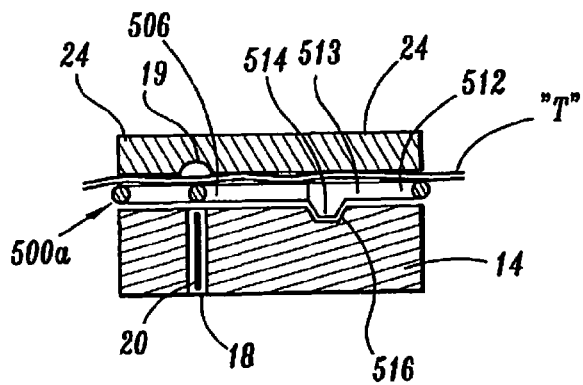
FIG. 14
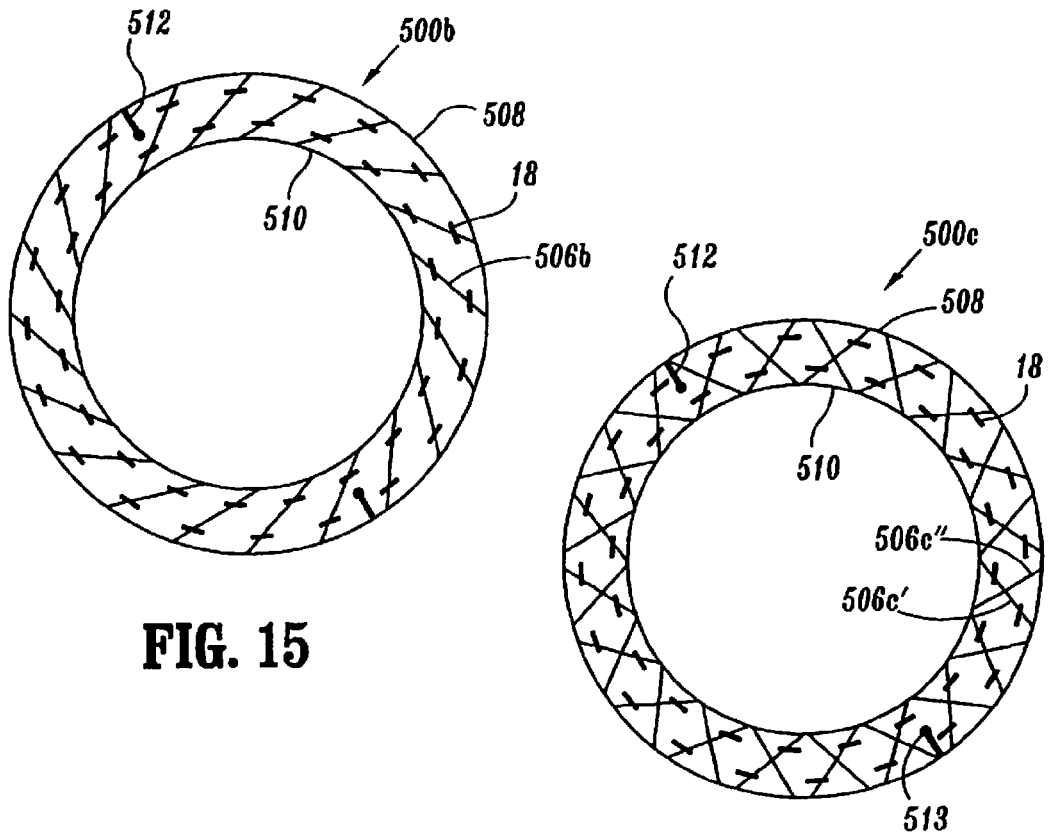
FIG. 15
FIG. 16

ANNULAR SUPPORT STRUCTURES

CROSS-REFERENCE TO RELATED APPLICATIONS

The present application is a Continuation Application that claims the benefit of and priority to U.S. patent application Ser. No. 11/872,778, filed on Oct. 16, 2007, now U.S. Pat. No. 7,951,166, which is a Continuation Application that claims the benefit of and priority to U.S. patent application Ser. No. 10/516,435, filed on Nov. 30, 2004, now U.S. Pat. No. 7,744,627, which is a U.S. National Stage Application that claims benefit under 35 U.S.C. §371(a) of International Application Serial No. PCT/US03/19331, filed on Jun. 17, 2003, that claims the benefit of and priority to U.S. Provisional Patent Application Ser. No. 60/389,567 filed on Jun. 17, 2002, now abandoned, the entire contents of which are incorporated herein by reference.

BACKGROUND

1. Technical Field

The present disclosure relates to annular support structures and, more particularly, to reinforcing lumen rings, for use in conjunction with a circular endoscopic stapling instrument, for maintaining the resulting anastomotic lumen in an open condition.

2. Background of Related Art

Staples have traditionally been used to replace suturing when joining or anastomosing various body structures, such as, for example, the bowel or bronchus. The surgical stapling devices employed to apply these staples are generally designed to simultaneously cut and seal an extended segment of tissue in a patient, thus, vastly reducing the time and risks of such procedures.

Linear surgical stapling devices are employed by surgeons to sequentially or simultaneously apply one or more linear rows of surgical fasteners, e.g., staples or two-part fasteners, to body tissue for the purpose of joining segments of body tissue together. Such devices generally include a pair of jaws or finger-like structures between which body tissue to be joined is placed. When the stapling device is actuated and/or "fired" firing bars move longitudinally and contact staple drive members in one of the jaws, surgical staples are pushed through the body tissue and into/against an anvil in the opposite jaw thereby crimping the staples closed. If tissue is to be removed, a knife blade can be provided to cut between the rows/lines of staples. Examples of such instruments are described in U.S. Pat. Nos. 4,354,628, 5,014,899 and 5,040,715, the entirety of each of which is incorporated herein by reference.

For most procedures, the use of bare staples, with the staples in direct contact with the patient's tissue, is generally acceptable. The integrity of the tissue will normally serve to prevent the staples from tearing out of the tissue and compromising the sealing before healing has occurred. However, in some surgical operations, surgical supports, e.g., meshes, are employed by surgeons to bridge, repair and/or reinforce tissue defects with a patient, especially those occurring in the abdominal wall, chest wall, diaphragm and other musculoaponeurotic areas of the body. Examples of surgical supports are disclosed in U.S. Pat. Nos. 3,054,406, 3,124,136, 4,347,847, 4,655,221, 4,838,884 and 5,002,551.

When the staples are applied in surgical operation utilizing surgical supports (i.e., reinforcing material), the legs of the staple typically pass from the cartridge jaw through a layer of reinforcing material, then through the patient's tissue before encountering the anvil jaw. In an alternative procedure, the legs of the staple typically pass from the cartridge jaw through a first layer of reinforcing material, then through the patient's tissue, and finally through a second layer of reinforcing material before encountering the anvil jaw. With the staples in place, the stapled tissue is clamped between the layers of reinforcing material.

While the surgical supports described above are used in conjunction with linear surgical staplers, the need exists for a support structure for use in conjunction with an annular surgical stapler, for example, an end-to-end anastomosis stapler such as a Model "EEA™" instrument available from United States Surgical, a Division of Tyco Health-Care Group, LP, Norwalk, Conn. and disclosed in U.S. Pat. No. 5,392,979 to Green et al. In general, an end-to-end anastomosis stapler typically places an array of staples into the approximated sections of a patient's bowels or other tubular organs. The resulting anastomosis contains an inverted section of bowel which contains numerous "B" shaped staples to maintain a secure connection between the approximated sections of bowel.

One possible side effect of any end-to-end bowel anastomosis is its tendency to stenos over time, which stenosis can decrease the diameter of the lumen over time. Accordingly, the need exists for a surgical support structure which operates in conjunction with any end-to-end anastomosis device and assists in maintaining the lumen of the anastomosed bowel or other tubular organ open over time.

SUMMARY

The present application is directed in part to support structures configured and adapted for use in conjunction with a circular stapling instrument having a staple cartridge assembly and an anvil assembly. The support structures are rigid or semi-rigid and are adapted to maintain a resulting anastomotic lumen, formed by the circular stapling apparatus, in an open condition.

The support structures can include an annular ring which is attachable and/or connectable to the distal-most surface of the staple cartridge assembly by, for example, use of an adhesive disposed between the annular ring and the distal-most surface of the staple cartridge assembly, frictional engagement between at least one projection extending from the surface of the annular ring and at least one corresponding complementary recess formed in the distal-most surface of the staple cartridge assembly.

It is envisioned that the annular ring can be provided with a plurality of slots formed therein which substantially correspond to the staple slots of the staple cartridge assembly.

The annular ring can be formed of a rigid mesh-like material, defining a plurality of interstitial spaces through which the legs of the staples are to pass. Preferably, the annular ring is connected and/or attached to the distal-most surface of staple cartridge assembly such that the legs and/or strands of the mesh overlie and/or traverse the staple slots, more preferably, the legs and/or strands extend substantially across the central portion of the staple slots (i.e., between the legs of the staples disposed in the staple slots). The legs and/or strands of the mesh intersect at least one, preferably a plurality of staple slots.

The mesh can be formed in any suitable configuration, e.g. a radial pattern, an annular zig-zag pattern, an annular wave/sinusoidal pattern, a cris-cross pattern and the like. Preferably, the annular ring includes an outer annular band and an inner annular band.

The annular ring can include a cartridge orientation member which is configured and dimensioned to axially align the annular ring with respect to the staple cartridge assembly and to radially orient the annular ring with respect to the staple slots (e.g., so that the strands of the mesh extend across the staple slots). The cartridge orientation member can include at least one arm extending radially from at least one of the inner and outer annular band and a nub formed on an end of the arm(s). The nubs preferably engage corresponding complementary recess formed in the distal-most surface of the staple cartridge assembly to thereby frictionally connect the annular ring to the staple cartridge assembly. It is envisioned that adhesive can be provided to the distal-most surface of the staple cartridge assembly and/or to the recesses formed in the distal-most surface of the staple cartridge assembly to enhance the connection of the annular ring to the staple cartridge assembly.

In a preferred embodiment rigid support structure includes a rigid annular ring configured and adapted to substantially overlie at least one annular arrangement of staples of the staple cartridge assembly. The annular ring can include an outer annular wall having a diameter, an inner annular wall spaced a radial distance inward of the outer annular wall and defining a space, an upper wall interconnecting the outer annular wall and the inner annular wall, and a lower wall spaced a distance from the upper wall and interconnecting the outer annular wall and the inner annular wall, the outer annular wall. The inner annular wall and the upper and lower walls define an interior reservoir. The support structure further includes a wound closure material retained in the reservoir.

The diameter of the outer annular wall is preferably substantially equal to an outer diameter of the staple cartridge assembly and the diameter of the inner annular wall is radially inward of the at least one annular arrangement of staples.

The annular ring can have a circular, rectilinear, ovular, triangular and arcuate cross-sectional profile.

The support structure can further include a support spoke integrally connected to and extending diametrically across the inner annular wall. It is envisioned that the anvil assembly includes an elongated shaft. The support spoke includes a central hub having a central axial opening formed therethrough, wherein the central axial opening is configured and dimensioned to receive the shaft of the anvil assembly therethrough.

Preferably, the wound closure material is at least one of an adhesive, a hemostat and a sealant. The adhesive can include albumin/glutaraldehyde materials, protein derived materials, and cyanoacrylate-based materials. The sealant can include fibrin based materials, collagen-based materials, synthetic polymer-based materials, synthetic polyethylene glycol-based materials, and hydrogel materials. The hemostat can include fibrin-based materials, collagen-based materials, oxidized regenerated cellulose-based materials, gelatin-based materials, and fibrinogen-thrombin combination materials.

It is envisioned that at least one of the annular outer wall and the annular inner wall is made of a rigid material. The rigid material can include stainless steel and titanium. The rigid material can further include a bioabsorbable material.

It is contemplated that the rigid annular ring includes a plurality of interstitial spaces extending therethrough, the spaces being configured and adapted to allow the legs of the staples to pass through the spaces.

The rigid annular ring can have a plurality of cartridge orientation members adapted to orient the spaces of the annular support structure to radially and circumferentially overlie the staple slots of the staple cartridge assembly. The cartridge orientation members can be a plurality of nubs extending therefrom, wherein the nubs are spaced from each other and are adapted and configured to engage complementary recesses formed in the distal end surface of the staple cartridge assembly.

The present application is directed to a method for reinforcing an anastomotic lumen of a hollow body. The method includes the step of cutting the hollow body into a pair of severed sections, inserting an anvil assembly of a circular stapling apparatus into one of the pair of severed sections of the hollow body such that a shaft of the anvil assembly extends out of a terminal end of one of the pair of severed sections, suturing the terminal end of one of the pair of severed sections around the shaft of the anvil assembly, inserting a staple cartridge assembly into the other of the pair of severed sections such that the open end of the cartridge assembly faces the open end of the severed sections of the hollow body, suturing the terminal end of the other of the pair of severed sections, providing a rigid reinforcing lumen ring between the anvil assembly and the staple cartridge assembly such that when the circular stapling apparatus is fired, surgical staples penetrate the terminal ends of the pair of severed sections and the reinforcing lumen ring, coupling and approximating the anvil assembly to the staple cartridge assembly, and firing the circular stapling apparatus.

The method can further include providing the reinforcing lumen ring between the terminal ends of the pair of severed sections. The method can include providing the reinforcing lumen ring between the anvil assembly and the pair of severed sections. The method can include providing the reinforcing lumen ring between the staple cartridge assembly and the other of the pair of severed sections. Preferably, the reinforcing lumen ring is centrally aligned with the anvil assembly and staple cartridge assembly.

The method can further include the step of orienting and aligning the reinforcing lumen ring with the staple cartridge assembly. The reinforcing lumen ring includes interstitial spaces defined by a plurality of legs extending substantially in a radial direction, wherein a plurality of the legs traverse preferably a central portion of a plurality of staple slots of the staple cartridge assembly.

It is an object of the present disclosure to provide a supporting structure, in the form of a ring, for reinforcing or providing increased structural integrity to an anastomotic lumen.

It is an additional object of the present disclosure to provide a reinforcing lumen ring which will prevent or suppress the incidence of stenosis at or along the anastomotic site.

It is a further object of the present disclosure to provide a reinforcing lumen ring configured and adapted to receive the fired staples of a circular endoscopic stapling apparatus.

These and other objects will be more clearly illustrated below by the description of the drawings and the detailed description of the preferred embodiments.

BRIEF DESCRIPTION OF THE DRAWINGS

By way of example only, preferred embodiments of the disclosure will be described with reference to the accompanying drawings, in which:

FIG. 1 is an enlarged perspective view, with portions broken away, of a distal end of an annular circular stapling apparatus illustrating the placement of a support structure, in accordance with the present disclosure, between the anvil and the staple cartridge of the stapling apparatus;

FIG. 2 is a cross-sectional side elevational view of a pair of approximated bowels anastomosed together and including the support structure shown in FIG. 1 stapled to an end surface thereof;

FIG. 11 is a top plan view of yet another embodiment of a support structure in accordance with the present disclosure;

FIG. 12 is a top plan view of still another embodiment of a support structure in accordance with the present disclosure as seen placed in an overlied position over the distal end surface of the staple cartridge;

FIG. 13 is a cross-sectional view through section C-C of FIG. 12;

FIG. 14 is a cross-sectional view through section D-D of FIG. 12;

FIG. 15 is a top plan view of yet another embodiment of a support structure in accordance with the present disclosure;

FIG. 16 is a top plan view of still another embodiment of a support structure in accordance with the present disclosure;

DETAILED DESCRIPTION OF PREFERRED EMBODIMENTS

Figure 3:
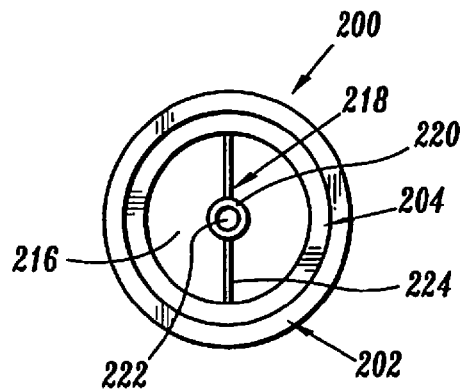
FIG. 3 is a top plan view of a support structure in accordance with an alternative embodiment of the present disclosure.

Preferred embodiments of the presently disclosed support structure will now be described in detail with reference to the drawing figures wherein like reference numerals identify similar or identical elements.

Referring initially in detail to FIG. 1, a surgical stapling support structure in the form of a lumen reinforcing ring, in accordance with an embodiment of the present disclosure, is generally shown as 100. Reinforcing ring 100 includes an annular ring 102 defined by an outer terminal edge 104, an inner terminal edge 106, an upper surface 108 and a lower surface 110. Inner terminal edge 106 of reinforcing ring 100 defines a central opening 112.

As seen in FIG. 1, reinforcing ring 100 cooperates with a circular stapling apparatus 10. Stapling apparatus 10 includes an elongated neck 12 having a staple cartridge assembly 14 operatively coupled to an end thereof and an anvil assembly 16 configured and adapted to removably engage the distal end of staple cartridge assembly 14. Staple cartridge assembly 14 is configured and adapted to expel an annular array of staples 20 (see FIG. 2) out of the distal end thereof. Preferably, staple cartridge assembly 14 includes a plurality of annular rows of staple slots 18 having staples 20 therein. Anvil assembly 16 includes a shaft 22 which is adapted to be releasably mounted within staple cartridge assembly 14 and an anvil 24 which is mounted on shaft 22 and is oriented to be positioned towards the distal end of staple cartridge assembly 14. Anvil 24 is provided with an annular array of staple forming cups 19 (see FIG. 13), conforming to the number of annular rows and number of staple slots 18, the cups being configured and adapted to form staples 20, e.g. into a B-shape, as they are expelled from staple cartridge assembly 14.

Reinforcing ring 100 is releasably attached to either anvil assembly 16 or staple cartridge assembly 14. Alternatively, anvil assembly 16 and staple cartridge assembly 14 can both have a reinforcing ring 100 disposed thereon (not shown) to provide a tissue/support "sandwich" upon actuation and/or firing of stapling apparatus 10.

The attachment of reinforcing ring 100, to circular stapling apparatus 10 should be secure enough to prevent reinforcing ring 100 from slipping off of stapling apparatus 10, yet not be so strong as to inhibit separation of reinforcing ring 100 from stapling device 10 after stapling device 10 has been actuated. Such releasable attachment can advantageously be effected by employing a plurality of pins as described in commonly assigned U.S. Pat. No. 5,542,594, the entire contents of which are incorporated herein by reference. It is further contemplated that an adhesive, for example, a releasable adhesive, or a plurality of longitudinally spaced clips (not shown herein) may also be employed as the means for securing reinforcing ring 100 to stapling apparatus 10. A combination of pins, clips and/or adhesive(s) can also be employed. The precise number and location of pins and/or clips or the amount or placement of continuity of spots or lines of adhesive is not critical so long as reinforcing ring 100 is releasably attached to stapling apparatus 10.

With reference to FIGS. 1 and 2, the preferred method of use of support structure 100, in an anastomotic surgical operation, will now be described. After having cut the hollow organ of the patient (e.g., the bowel or intestine), anvil assembly 16 is inserted into an end of a severed section of the intestine, using known surgical techniques, such that shaft 22 extends out of the open end of the intestine or bowel "B". Anvil assembly 16 is preferably secured in place at the free end of the intestine by using a purse string type suture to cinch the end of the hollow organ around shaft 22. Staple cartridge assembly 14 of apparatus 10, having reinforcing ring 100 operatively coupled to the distal surface thereof, is inserted into either another incised area of the intestine or bowel "B" or an opening of the patient, and the free end of the other severed section of the intestine is purse-string sutured leaving a small opening for passage of shaft 22 therethrough.

Shaft 22 is passed through the small opening and operatively coupled to staple cartridge assembly 14 and anvil assembly 16 is drawn toward staple cartridge assembly 14. When the distance between staple cartridge assembly 14 and anvil assembly 16 has reached an appropriate value for anastomosis, stapling apparatus 10 is actuated or fired. When apparatus 10 is fired, staples 20 are expelled from staple cartridge assembly 14, such that their legs pass through reinforcing ring 100, through both layers of purse stringed intestines, and are clinched against the anvil deforming cups. At the same time, the excess tissue, radially inward of the innermost staple line, is severed off with a cylindrical cutter. (not shown).

The resultant anastomosis will have an annular support structure (i.e., reinforcing ring 100) at the site of the stapled connection. Reinforcing ring 100 gives the anastomosis more structural integrity by effectively providing a "backbone" which aides in maintaining the lumen at the anastomosis sight open.

It is contemplated that rigid reinforcing ring 100 can be made from or comprised of a surgical grade mesh. The mesh would allow the legs of staples 20 to pass freely through reinforcing ring 100 and into the adjacent body tissue of the hollow body organ. It is further contemplated that reinforcing ring 100 is made from a biocompatible non-absorbable (i.e., permanent) material, such as polytetrafluoroethylene (PTFE), for example, "TEFLON", which is a registered trademark owned by DuPont de Nemours & Co., or a biocompatible absorbable material. The biocompatible materials can be woven, knit, or non-woven. Bio-absorbable materials include those fabricated from homopolymers, copolymers or blends obtained from one or more monomers selected from the group consisting of glycolide, glycolic acid, lactide, lactic acid, p-dioxanone, α-caprolactone and trimethylene carbonate. Non-absorbable materials include those that are fabricated from such polymers as polyethylene, polypropylene, nylon, polyethylene terephthalate, polytetrafluoroethylene, polyvinylidene fluoride, and the like. Further non-absorbable materials include and are not limited to stainless steel, titanium and the like. It is preferred that the annular support structure be or be comprised of a mesh and it is preferred that the mesh be comprised of biocompatible titanium and be rigid at least to prevent radially inward stenos of reinforcing ring 100. As will be described in greater detail below, the mesh allows staple legs to pass through the plane of the support structure while the back spans of a plurality of staples engage a strand or strands of the mesh and do not pass through the annular support member.

It is further contemplated that reinforcing ring 100 is made from or comprised of a medical grade bio-absorbable material, for example, Polyglycolic Acid (PGA) and Polylactic Acid (PLA). For example, it is preferable that reinforcing ring 100 remains in place for approximately 2-3 weeks in order for the anastomosis to sufficiently heal prior to reinforcing ring 100 being absorbed into the body.

It is further contemplated that reinforcing ring 100 can act as an adhesion barrier, hemostatic agent, reinforcement, tissue growth enhancer, and the like. Furthermore, it shall be understood that reinforcing ring 100 can have incorporated therein and/or thereon one or more medically and/or surgically useful substances such as drugs, enzymes, growth factors, peptides, proteins, dyes, diagnostic agents or hemostasis agents or any other pharmaceutical used in the prevention of stenosis.

Figure 4:
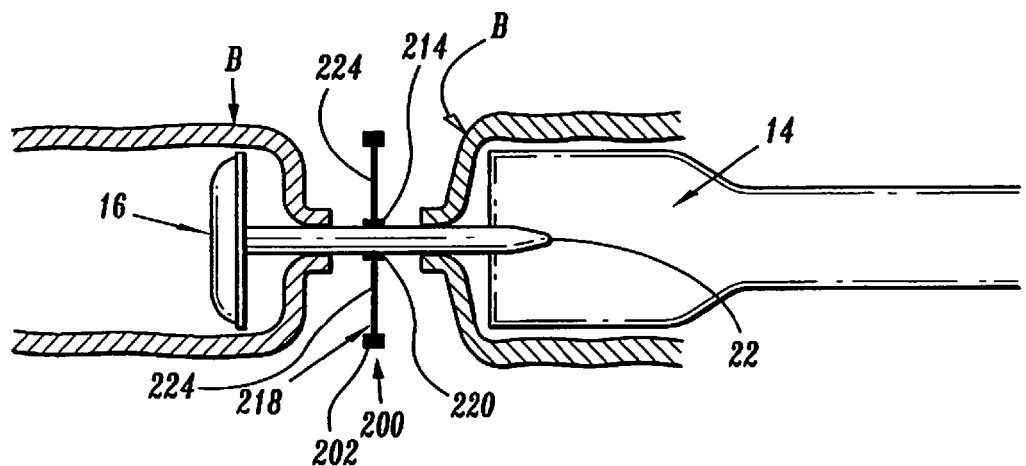
FIG. 4 is a cross-sectional side elevational view, with portions broken away, of end portions of a bowel, illustrating the positioning of portions of a circular stapling apparatus within the end portions of the bowels prior to approximation, and of the support structure of FIG. 3 about the anvil shaft between the end portions of the bowel.
Figure 5:
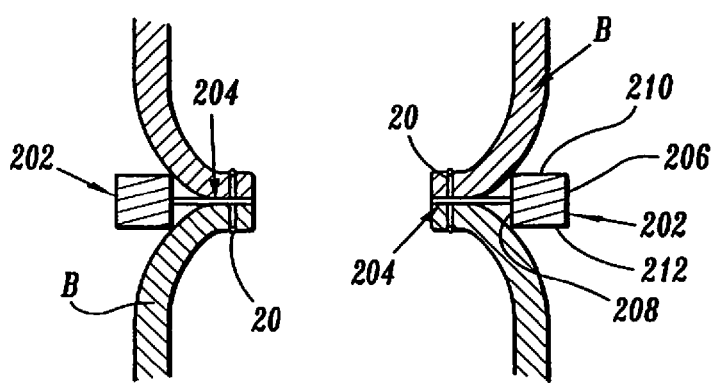
FIG. 5 is a cross-sectional side elevational view of the end portions of the bowels of FIG. 4, after they are anastomosed together and stapled with the support structure of FIG. 3, therebetween.

Turning now to FIGS. 3-5, an alternative embodiment of a support structure in the form of a lumen reinforcing ring, in accordance with the present disclosure, is shown generally as 200. Reinforcing ring 200 includes a radial outer ring 202, a radial inner ring 204 and a support spoke 218. Radial outer ring 202 includes an outer terminal surface 206, an inner terminal surface 208, an upper surface 210 and a lower surface 212, respectively, defining a rectangular cross-sectional profile as seen in FIG. 5. While a rectangular profile is disclosed, it is envisioned that radial outer ring 202 can have any cross-sectional profile, such as, for example, circular, ovoid, triangular, arcuate, etc. In a preferred embodiment, radial outer ring 202 is made from a rigid or, less preferably, a semi-rigid material which is either bioabsorbable or non-bioabsorbable.

Reinforcing ring 200 further includes a radial inner ring 204 integrally extending from inner terminal surface 208 of radial outer ring 202 and terminating in an inner terminal edge 214. Inner terminal edge 214 of reinforcing ring 200 defines a central opening 216. It is contemplated that radial inner ring 204 be made from or comprised of a rigid, semi-rigid or non-rigid material which is either bioabsorbable or non-bioabsorbable. While a non-rigid material such as a surgical mesh integrally formed into annular outer ring 202 is contemplated, it is preferred that radial inner ring 204 be made from a rigid or semi-rigid material so that support spoke 218 can be securely attached thereto.

Preferably, radial outer ring 202 has in inner diameter slightly larger than an outer diameter of staple cartridge assembly 14. In this manner, support structure 200 can be seated at the distal end of staple cartridge assembly 14 such that radial inner ring 204 rests against the distal end surface of staple cartridge assembly 14. Preferably, radial inner ring 204 has a radial extent or width which is sufficient to at least extend over all of the plurality of rows of staples 18 of staple cartridge assembly 14. In this manner, when staples 20 are fired out of staple cartridge assembly 14, the legs of staples 20 will pass through radial inner ring 204.

Reinforcing ring 200 further includes a support spoke 218 having a central hub 220 disposed within central opening 216. Preferably, central hub 220 and central opening 216 share a common central axis. Central hub 220 defines a central opening 222 extending therethrough, wherein central opening 222 is of a sufficient size to permit passage of shaft 22 of anvil assembly 16 therethrough. Support spoke 218 preferably extends diametrically across reinforcing ring 200 and includes a central hub 220. Preferably, supporting arms 224 are attached to inner terminal edge 214 in such a manner that support spoke arrangement 218 can break away and be removed from support structure 200. While a pair of support arms 224 have been shown and described, it is contemplated and within the scope of the present disclosure that any number of arms can be provided.

With reference to FIGS. 4 and 5, the preferred method of use of reinforcing ring 200, in an anastomotic surgical operation, will now be described. After having cut the hollow organ of the patient (i.e., the bowel or intestine), anvil assembly 16 is inserted into an end of a severed section of the intestine, using known surgical techniques, such that shaft 22 extends out of the end of the intestine or bowel "B". Anvil assembly 16 is preferably secured in place at the end of the intestine by using a purse string type suture to cinch the end of the hollow organ around shaft 22. Support structure 200 is then placed on shaft 22 such that shaft 22 is fed through central opening 222 of central hub 220 of support spoke 218. Staple cartridge assembly 14 of apparatus 10 is then inserted into either another incised area of the intestine or an opening of the patient and the other end of the severed section of the intestine is purse-string sutured leaving a small opening for passage of shaft 22 therethrough, as seen in FIG. 4.

Shaft 22 is passed through the small opening and operatively coupled to staple cartridge assembly 14, and anvil assembly 16 is drawn toward staple cartridge assembly 14. When the distance between staple cartridge assembly 14 and anvil assembly 16 has reached an appropriate value for anastomosis, stapling apparatus 10 is fired. When apparatus 10 is fired, staples 20 are expelled from staple cartridge assembly 14, such that their legs pass through a first layer of intestinal tissue, through annular inner ring 204 and through a second layer of intestinal tissue. The legs of staples 20 are then clinched against the anvil forming cups 19. At the same time, the excess tissue radially inward of the innermost staple line, as well as the diametrically opposed supporting arms 224, is severed off with a cylindrical cutter (not shown), resulting in an open intestinal lumen as seen in FIG. 5.

Reinforcing ring 200 helps to maintain the lumen of the hollow organ (i.e., intestine) open over time and to counteract the effects of stenosis. With radial inner ring 204 secured to the anastomosed hollow organ, radial outer ring 206 acts like a buttress to prevent the collapse of the anastomosed hollow organ due to stenosis. In other words, since the hollow body organ is anchored to radial inner ring 204 of reinforcing ring 200, as the hollow body organ tends to retract radially inward due to stenosis, reinforcing ring 200 retains its shape (i.e., effectively counter acting the radially inward pull of the stenosing hollow body organ), thereby keeping the lumen through the hollow body organ open.

Figure 6:
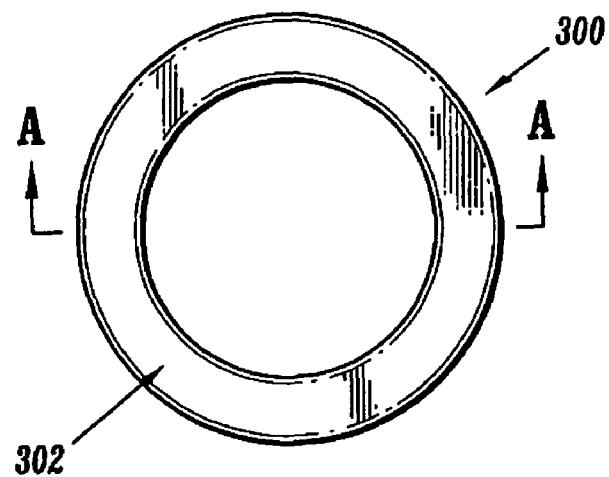
FIG. 6 is a top plan view of an alternative embodiment of a support structure in accordance with the present disclosure.
Figure 7:
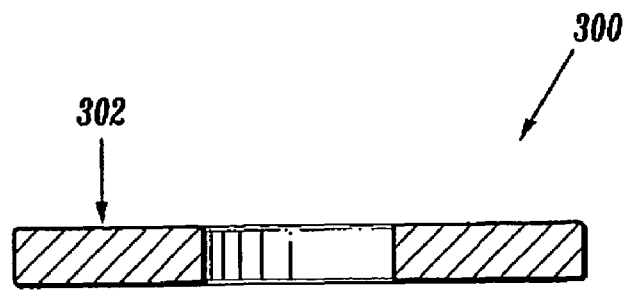
FIG. 7 is a cross-sectional side elevational view of the support structure of FIG. 6, taken along line A-A.
Figure 8:
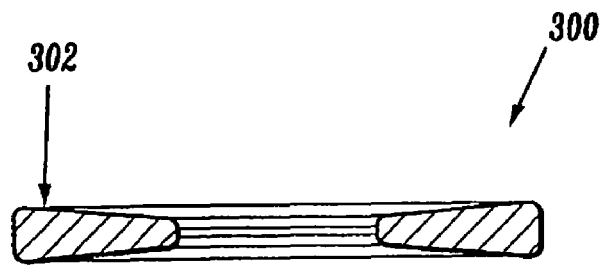
FIG. 8 is a cross-sectional side elevational view of an alternative embodiment of the support structure of FIG. 6, as would be seen along line A-A.

Turning now to FIGS. 6-8, an alternative embodiment of a support structure in the form of a lumen reinforcing ring, in accordance with the present disclosure, is shown generally as 300. Reinforcing ring 300 includes an annular ring 302 having a rectangular cross-section as seen in FIG. 7. When using a support structure having a rectangular cross-section, it is envisioned that a surgical stapler 10 has an outer annular rim, an inner annular rim or both extending from or at the distal end thereof (not shown). Accordingly, inner and/or outer annular rims ensure that reinforcing ring 300 is properly seated on the end of surgical stapler 10.

While a generally rectangular cross-section is shown in FIG. 7, it is envisioned that annular ring 302 of reinforcing ring 300 can have a generally triangular cross-sectional profile as seen in FIG. 8. Preferably, a support structure having a triangular cross-sectional profile is used, in connection with a staple cartridge assembly having a tapered distal surface for cooperating and mating with a tapered surface of reinforcing ring 300, as well as having an anvil having a tapered proximal surface for cooperating and mating with the opposite surface of the support structure be used. Accordingly, as the anvil assembly is drawn toward the staple cartridge assembly, the tapered surfaces cooperate with one another to cause the support structure to automatically centrally align itself on the end of the surgical stapler.

Preferably, as seen in FIG. 8, annular ring 302 has a larger thickness at the outer terminal edge and a smaller thickness at the inner terminal edge thereof. However, it is envisioned that the support structure can have an annular ring in which the inner terminal edge has a larger thickness than the outer terminal edge.

Figure 9:
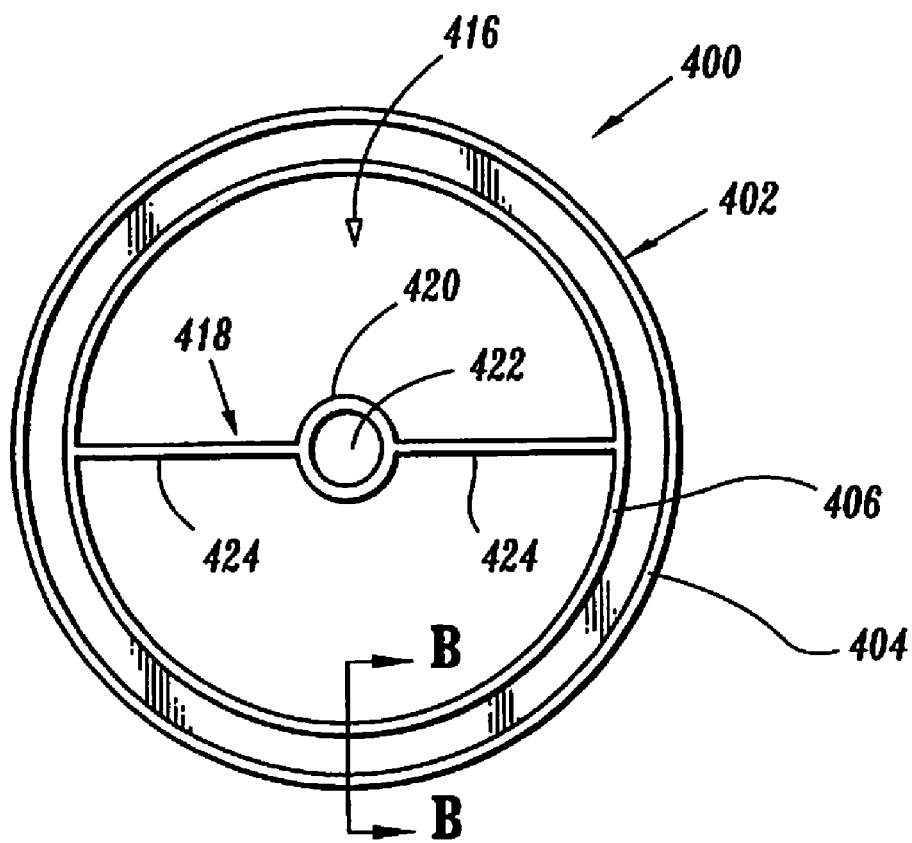
FIG. 9 is a top plan view of an alternative embodiment of a support structure in accordance with the present disclosure.
Figure 10:
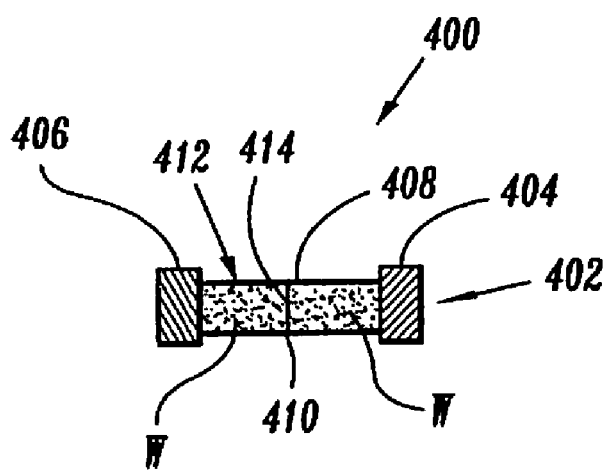
FIG. 10 is a cross-sectional side elevational view of an alternative embodiment of the support structure shown in FIG. 9, taken along line B-B.

Referring now to FIGS. 9 and 10, an alternative embodiment of a support structure in the form of a lumen reinforcing ring, in accordance with the present disclosure, is shown generally as 400. Reinforcing ring 400 includes a radial ring 402 having a radial outer wall 404, a radial inner wall 406 and an upper and a lower wall 408 and 410, respectively, interconnecting radial outer wall 404 to radial inner wall 406. Radial inner wall 406 defines a central opening 416 therein. Radial outer wall 404, radial inner wall 406, upper wall 408 and lower wall 410 define a reservoir 412. Preferably, upper and lower walls 408 and 410 have a width which is at least equal to or slightly larger than the width of the plurality of rows of staples 20 of staple cartridge assembly 14.

In a preferred embodiment, reservoir 412 retains an amount of a biological adhesive therein. While a biological adhesive has been disclosed as being retained within reservoir 412, it is envisioned that reservoir 412 can retain any type of wound closure material "W" therein. It is envisioned that wound closure material "W" can include one or a combination of adhesives, hemostats, and sealants. Surgical biocompatible wound closure materials which can be retained in reservoir 412 include adhesives whose function is to attach or hold organs, tissues or structures, sealants to prevent fluid leakage, and hemostats to halt or prevent bleeding. Examples of adhesives which can be employed include protein derived, aldehyde-based adhesive materials, for example, the commercially available albumin/glutaraldehyde materials sold under the trade designation BioGlue™ by Cryolife, Inc., and cyanoacrylate-based materials sold under the trade designations Indermil™ and Derma Bond™ by Tyco Healthcare Group, LP and Ethicon Endosurgery, Inc., respectively. Examples of sealants, which can be employed, include fibrin sealants and collagen-based and synthetic polymer-based tissue sealants. Examples of commercially available sealants are synthetic polyethylene glycol-based, hydrogel materials sold under the trade designation CoSeal™ by Cohesion Technologies and Baxter International, Inc. Examples of hemostat materials, which can be employed, include fibrin-based, collagen-based, oxidized regenerated cellulose-based and gelatin-based topical hemostats. Examples of commercially available hemostat materials are fibrinogen-thrombin combination materials under sold the trade designations CoStasis™ by Tyco Healthcare Group, LP, and Tisseel™ sold by Baxter International, Inc. Hemostats herein include astringents, e.g., aluminum sulfate, and coagulants.

The preferred method of use of reinforcing ring 400 is similar to the method of use of support structure 100 and will only be discussed in detail to the extent necessary to identify differences therebetween.

Accordingly, when apparatus 10 is fired, staples 20 are expelled from staple cartridge assembly 14, pass through a first layer of intestinal tissue, through upper and lower wall 408, 410, respectively, thereby releasing wound closure material "W" from within reservoir 412 of reinforcing ring 400, and through a second layer of intestinal tissue. The legs of staples 20 are then clinched against the anvil deforming cups. At the same time, the excess tissue radially inward of the innermost staple line, as well as the diametrically opposed supporting arms 424, are severed off with a cylindrical cutter (not shown), resulting in an open intestinal lumen as seen in FIG. 5.

It is envisioned that reinforcing ring 400 can be fabricated without a support spoke 418. In such an embodiment, annular ring 402 can be configured and dimensioned such that annular outer wall 404 is radially larger than the distal end of staple cartridge assembly 14 and annular inner wall 406 is radially smaller than the distal end of the staple cartridge assembly 14. In this manner, reinforcing ring 400 is configured and dimensioned to sit on the distal end of staple cartridge assembly 14 such that upper and lower walls 408, 410, respectively, overlie the distal end surface of staple cartridge assembly 14.

Preferably, reservoir 412 is hermetically sealed with a staple leg penetrable and/or rupturable material, such as, for example, a thin film or membrane.

Optionally, reservoir 412 can be divided into any number of reservoirs by providing annular dividing walls 414 disposed between annular outer wall 404 and annular inner wall 406. In this manner, reinforcing ring 400 can retain more then one wound closure material "W", such as, for example, a combination of an adhesive, an astringent and/or a hemostat.

Preferably, some portion of the support structure of the invention, preferably annular outer wall 404 and/or inner annular wall is fabricated from a rigid material including, but not limited to, stainless steel and titanium.

Turning now to FIG. 11, an alternative embodiment of a support structure is shown generally as 500. As seen in FIG. 11, support structure 500 is in the form of a triangular or wave patterned annular ring having peripheral peaks 502 and radially inner valleys 504 joined by legs 506. As seen in the top plan view, a plurality of legs 506 traverse or intersect preferably a central portion (that is not where the legs of staples 20 are ejected from) of a plurality of, preferably each of cartridge staple slots 18. In use, support structure 500 is to be laid against and/or positioned to overlie and releasably attached to the distal end surface of the staple cartridge assembly 14 in such a manner that staples 20 will form around legs 506 when fired from staple cartridge assembly 14.

Turning now to FIGS. 12-14, a more rigid and more preferred modification of support structure 500 is shown as 500a. Support structure 500a is shown in position laying over the distal end surface of staple cartridge assembly 14. As seen in FIG. 12, peaks 502 are joined by a radially outer peripheral band 508 and valleys 504 are joined by a radially inner peripheral band 510. Support structure 500a preferably includes at least one, preferably a plurality of cartridge orientation members 511, here shown, e.g., as protrusions or nubs 514 depending from arm 512 attached to and extending radially inward from outer peripheral band 508. Nubs 514 can instead or also project from legs 506, peaks 502, valleys 504, and/or from inner peripheral band 510.

As seen in FIGS. 13 and 14, each cartridge orientation member 511 includes an arm 512 extending radially inward from outer peripheral band 508 and a nub 514 extending towards staple cartridge assembly 14 so as to engage at least one of, preferably a plurality of recesses or depressions 516 formed in the distal end surface of staple cartridge assembly 14. Preferably, nubs 514 are configured and dimensioned to complement recess 516 and create a friction-fit and/or snap-fit coupling therebetween. Nubs 514 cooperate with recesses 516 to connect support structure 500a to the distal-most surface of cartridge assembly 14. Nubs 514 and recesses 516 also radially and circumferentially orient or align support structure 500a over the distal end surface of staple cartridge assembly 14, so that legs 506 extend transversely across, transect or intersect staple slots 18.

As seen in FIGS. 12 and 13, legs 506, extending between radially outer band 508 and radially inner band 510, are oriented such that at least one leg 506, preferably a plurality of legs 506, extend transversely over staple slots 18 formed in staple cartridge assembly 14. Accordingly, as seen in FIGS. 13 and 14, when staples 20 are fired, the legs of staples 20 will form against staple forming cups 19 around leg(s) 506 and secure supporting structure 500a to tissue "T". In particular, the legs of staples 20 enter interstitial spaces 518, defined by legs 506, outer band 508 and inner band 510 of support structure 500a, in an unobstructed manner.

Preferably, radially outer band 508 and radially inner band 510 are fabricated from a rigid material (e.g., stainless steel, titanium, etc.). Legs 506 of support structure 500a can be formed from a non-rigid material (e.g., TEFLON, nylon, and the like), while legs 506 of support structure 500 are preferably formed from a rigid material (e.g., stainless steel, titanium, etc.).

Turning now to FIG. 15, a modified support structure 500b of support structure 500a is shown. Support structure 500b includes a radial array of legs 506b all oriented in substantially the same radial direction. Legs 506b are oriented between outer and inner bands 508, 510, respectively, such that legs 506b traverse over staple slots 18 formed in staple cartridge assembly 14. In this embodiment, legs 506b are preferably fabricated from a rigid material.

Turning now to FIG. 16, another modified support structure is shown as 500c. Support structure 500c includes a radial array of trans-secting legs 506c' oriented between outer and inner bands 508, 510, respectively, such that when support structure 500c is properly aligned legs 506c' traverse staple slots 18. Support structure 500c further includes a radial array of slot bypassing legs 506c'' oriented between outer and inner bands 508, 510, respectively, such that when support structure 500c is properly aligned legs 506c'' do not traverse staple slots 18.

Figure 17:
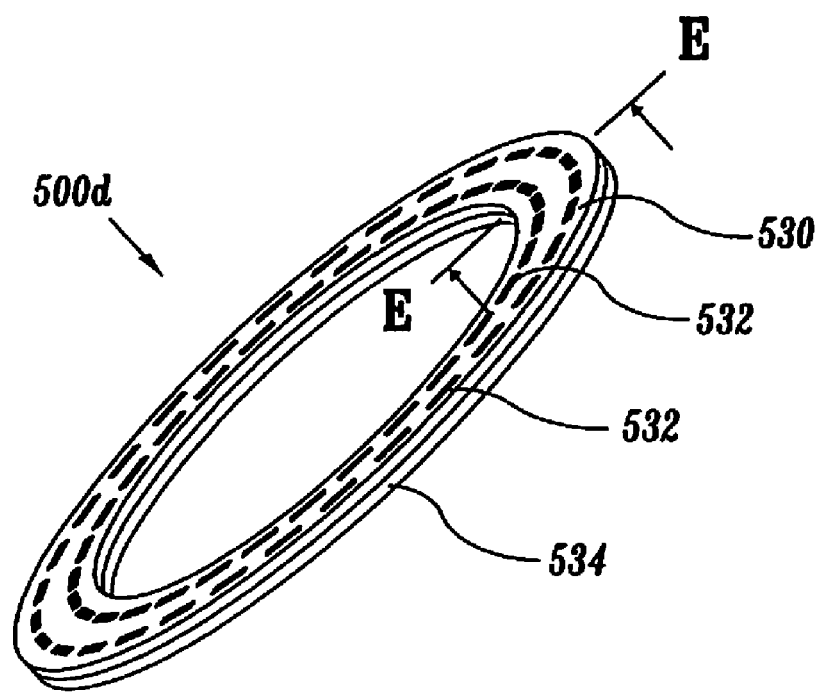
FIG. 17 is a perspective view of another embodiment of a support structure in accordance with the present disclosure.
Figure 18:
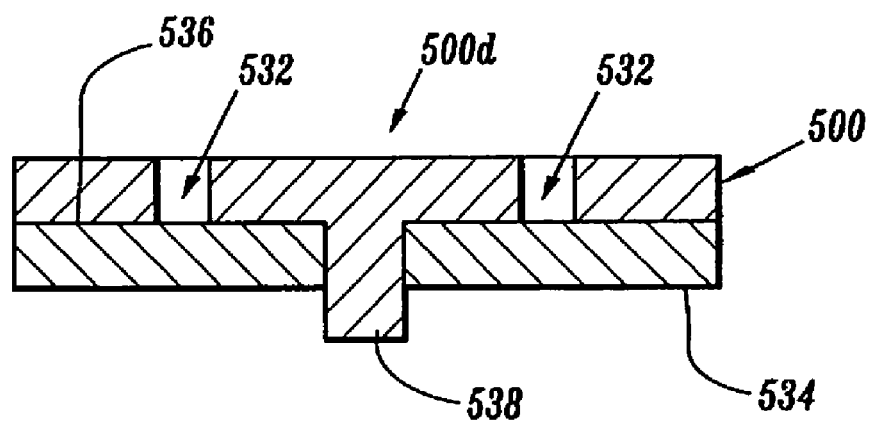
FIG. 18 is a cross-sectional view through E-E of FIG. 17.

Turning now to FIGS. 17 and 18, another modified support structure is shown as 500d. Support structure 500d includes an annular ring 530 including at least one, preferably a pair of annular rows of ring staple slots 532. Preferably, ring staple slots 532 are substantially identically positioned as staple slots 18 of staple cartridge assembly 14 (see FIG. 1). Annular ring 530 is preferably fabricated from a rigid material, such as, for example, stainless steel and/or titanium.

Support structure 500d preferably also includes an annular film or membrane 534 provided on a surface, preferable the proximal cartridge-facing surface 536. Membrane 534 preferably covers ring staple slots 534. Desirably, membrane 534 is made from TEFLON, however, it is envisioned that other materials can be used, such as, for example, any of the materials disclosed above. Desirably, a rigid, semi-rigid or flexible mesh can be employed instead of or in combination with membrane 534.

Support structure 500d further includes at least one, preferably a plurality of orientation members 538 (see FIG. 18) extending from surface 536 of annular ring 530. Orientation members 538 are preferably projections and/or nubs which extend from surface 536 of annular ring 530 and are configured and dimensioned to engage (e.g., frictionally, snap-fit, etc.) into recesses 516 (see FIGS. 12-14) formed in the distal-most surface of staple cartridge assembly 14.

In use, annular ring 530 is placed on the distal-most surface of staple cartridge assembly 14 such that membrane 534 is in contact with the distal-most surface of staple cartridge assembly 14. Accordingly, when staples 20 are fired, the legs of staples 20 will penetrate membrane 534 and form against forming cups 19, capturing membrane 534 and thereby securing annular ring 530 to tissue "T".

While support structure 500d has been shown and described as having a membrane 534 provided on the staple cartridge contacting side of annular ring 530, it is envisioned and within the scope of the present disclosure, that membrane 534 can be provided on the side opposite the staple cartridge contacting side of annular ring 530 or that a membrane 534 can be provided on both sides of annular ring 530.

It is envisioned that supporting structures including features and/or elements from any of the embodiments disclosed herein can be combined with one another and are thus included within the scope of the present disclosure.

Each of the above-described support structures are configured and adapted to aid in the prevention or suppression of the incidence of stenosis at the anastomotic site.

While the above disclosure has related generally to the anastomosis of intestines or bowels, it is clear that the support structures according to the present disclosure can be utilized in connection with the anastomosis of any type hollow body organ.

Further while the support structure has been disclosed herein in connection with certain embodiments and certain structural and procedural details, it is clear that changes, modifications or equivalents can be used by those skilled in the art. Therefore, the above description should not be construed as limiting, but merely as exemplifications of preferred embodiments. Those skilled in the art will envision other modifications within the scope and spirit of the present disclosure.

What is claimed is:

1. A system for joining a first body tissue and a second body tissue, the system comprising:
    a circular endoscopic stapling instrument having a staple cartridge assembly and an anvil assembly for approximating and joining a first body tissue to a second body tissue, and an elongated shaft extending between the staple cartridge assembly and the anvil assembly; and
    a reinforcing support structure supported on the shaft of the stapling instrument, the reinforcing support structure having a central hub for connection to the shaft of the stapling instrument and at least one annular reinforcing ring including a radial outer ring substantially coplanar with a radial inner ring, the at least one annular reinforcing ring supported on the central hub so that the at least one annular reinforcing ring is supported on the shaft at a location between the first body tissue and the second body tissue, wherein, after firing of the stapling instrument, the at least one annular reinforcing ring is interposed between and reinforces the joined first body tissue and the second body tissue.

2. The system according to claim 1, wherein the central hub is configured and dimensioned to frictionally engage the shaft of the stapling instrument.

3. The system according to claim 1, further comprising at least one support spoke integrally extending between the radial inner ring and the central hub.

4. The system according to claim 1, wherein the radial outer ring and the radial inner ring together define a reservoir therebetween.

5. The system according to claim 4, further comprising a wound closure material retained with the reservoir.

6. The system according to claim 5, wherein the reservoir is configured to rupture during a surgical procedure to expel the wound closure material between a first body tissue and a second body tissue.

7. The system according to claim 1, wherein
    the circular endoscopic stapling instrument has a plurality of annular rows of staples disposed in the staple cartridge assembly; and
    the at least one annular reinforcing ring has an inner terminal edge defining a central opening, the reinforcing ring having a radial extent extending about a width of the rows of staples.

8. The system according to claim 7, further comprising a support spoke extending between the central hub and the reinforcing ring.

9. A method of performing a surgical anastomotic procedure on a first body tissue and a second body tissue, the method comprising the steps of:
    providing a circular surgical stapling instrument including a staple cartridge assembly and an anvil assembly for approximating and joining the first body tissue to the second body tissue, and an elongated shaft extending between the staple cartridge assembly and the anvil assembly;
    providing a reinforcing support structure including at least one annular ring for reinforcing the first body tissue and the second body tissue after the anastomotic surgical procedure, the at least one annular ring including a radial inner ring circumscribed by and substantially level with a radial outer ring, and a central hub connected to the at least one annular ring, the central hub defining an opening configured and dimensioned to engage the shaft of the surgical stapling instrument at a location spaced an axial distance from a tissue contacting surface at the anvil assembly and spaced an axial distance from a tissue contacting surface of the cartridge assembly;
    securing the first body tissue to the anvil assembly;
    securing the second body tissue to the cartridge assembly;
    positioning the reinforcing support structure on the shaft of the surgical stapling instrument between the first body tissue and the second body tissue; and
    interconnecting the anvil assembly and the staple cartridge assembly via the shaft of the surgical stapling instrument such that the reinforcing support structure is interposed between the first body tissue and the second body tissue.

10. The method according to claim 9, further comprising the steps of:
    approximating the anvil assembly to the staple cartridge assembly; and
    firing the surgical stapling instrument.

11. The method according to claim 9, wherein the reinforcing support structure is centrally aligned with the anvil assembly and the staple cartridge assembly.

12. The method according to claim 9, wherein the radial outer ring and the radial inner ring together define a reservoir therebetween.

13. The method according to claim 12, further comprising a wound closure material retained with the reservoir.

14. The method according to claim 13, further comprising the step of:
    rupturing the reservoir during the surgical procedure to expel the wound closure material between a first body tissue and a second body tissue.

* * * * *